(12) United States Patent
Marks et al.

(10) Patent No.: US 8,771,596 B2
(45) Date of Patent: Jul. 8, 2014

(54) METHOD AND APPARATUS FOR STERILIZING INFECTIOUS MATERIAL

(75) Inventors: Daniel B. Marks, St. Louis, MO (US); Donald G. Fluchel, St. Louis, MO (US); Arda Kara, Brentwood, MO (US)

(73) Assignee: Progressive Recovery, Inc., Dupo, IL (US)

( * ) Notice: Subject to any disclaimer, the term of this patent is extended or adjusted under 35 U.S.C. 154(b) by 0 days.

(21) Appl. No.: 13/277,643

(22) Filed: Oct. 20, 2011

(65) Prior Publication Data
US 2012/0269678 A1 Oct. 25, 2012

Related U.S. Application Data

(60) Provisional application No. 61/405,979, filed on Oct. 22, 2010.

(51) Int. Cl.
*A61L 2/04* (2006.01)

(52) U.S. Cl.
USPC ............................ 422/26; 241/65; 241/606

(58) Field of Classification Search
USPC ................................ 422/26, 292; 241/65, 606
See application file for complete search history.

(56) References Cited

U.S. PATENT DOCUMENTS

| | | | | |
|---|---|---|---|---|
| 3,272,632 | A * | 9/1966 | Speer | 426/438 |
| 4,799,800 | A | 1/1989 | Schuler | |
| 5,217,688 | A * | 6/1993 | Von Lersner | 422/26 |
| 5,620,737 | A * | 4/1997 | Kazemzadeh | 426/641 |
| 6,348,174 | B1 | 2/2002 | Hall | |
| 7,767,142 | B1 * | 8/2010 | Smith et al. | 422/37 |
| 7,776,262 | B1 * | 8/2010 | Kodis | 422/28 |
| 2001/0009969 | A1 | 7/2001 | Kaye et al. | |
| 2005/0000108 | A1 * | 1/2005 | Ragnarsson | 34/92 |
| 2007/0199613 | A1 * | 8/2007 | Bouldin et al. | 141/73 |
| 2009/0311766 | A1 * | 12/2009 | Muth | 435/173.1 |

OTHER PUBLICATIONS

Auvermann et al. Carcass Disposal: A Comprehensive Review Chapter 4 Rendering. Mar. 2004. Report prepared by the National Agricultural Biosecurity Center Consortium Carcass Disposal Working Group.*

* cited by examiner

*Primary Examiner* — Sean E Conley
*Assistant Examiner* — Donald Spamer
(74) *Attorney, Agent, or Firm* — Mark E. Stallion; Husch Blackwell LLP (57) ABSTRACT

A method and apparatus for sterilization of infectious waste including animals, infected animal herds, infected human corpses and other infected material and proper disposal of resultant waste. The method and apparatus specifically relates to methods of safely sterilizing and disposing of infectious and non-infectious bio-waste in a cost effective manner.

12 Claims, 10 Drawing Sheets

METHOD AND APPARATUS FOR STERILIZING INFECTIOUS MATERIAL

CROSS REFERENCE

This application claims the benefit and priority of U.S. Provisional Patent Application Ser. No. 61/405,979, filed Oct. 22, 2010 entitled THERMAL TISSUE AUTOCLAVE, the entirety of which is incorporated herein by reference.

BACKGROUND OF INVENTION

1. Field of Invention

This invention relates generally to sterilization of infectious material and, more particularly, to sterilization of biological waste.

2. Background Art

Currently, universities, independent testing facilities and governmental agencies around the world produce or have political responsibility of large quantities of infectious animal waste due to research, study and containment. Additionally, future requirements to address pandemics can potentially add large numbers of animal carcasses and/or human cadavers which would require sterilization to insure containment of diseases.

Currently, the three methods commonly used in disposing of infectious waste such as infected animals or cadavers are incineration, burial and to a lesser extent alkaline hydrolysis. The known methods of disposal are faced with increasing regulations, including restrictions on waste water and land sites, environmental restrictions on air emissions, increased utility costs, as well as being faced with rising chemical costs in the case of using alkaline hydrolysis as a methodology. Thus, a less expensive and a more simplified approach to sterilizing and disposing of infectious material is needed, which is safe, more environmentally friendly and less expensive than existing sterilization methods and their subsequent disposal.

The various embodiments of the invention as described herein address the above issues and others.

BRIEF SUMMARY OF INVENTION

The present invention relates to the field of sterilization of infectious waste including animals, infected animal herds, infected human corpses and other infected material and to proper disposal of resultant waste. The invention relates to methods of safely sterilizing and disposing of infectious and non-infectious bio-waste in a cost effective manner.

One embodiment of the method of sterilizing a variety of infected material including animal and human corpses and/or parts includes the steps of providing a pressure holding vessel, loading the material into the vessel, heating the holding area of the vessel thereby energizing the material, for example, animal and/or human matter with external heat from either steam, electric, or other heat/energy source and agitating the material to effect size reduction of the material into a homogeneous, liquefied mixture. In one embodiment of the method the mixture can be heated to a temperature in the range of approximately 250 to 308 degrees F. at its equivalent saturated pressure and held approximately at that temperature for a period of approximately one to three hours to effect sterilization of the liquefied mixture. In one embodiment, the mixture can be cooled in the vessel and discharged.

One embodiment of the apparatus can include a vessel adapted for pressurization and having a heat source such a heating element heating a thermal fluid, powered by electrical current or other power source, that is operable to heat under pressure material placed in the chamber area of the vessel. One embodiment includes an agitator within the chamber of the vessel that is operable to agitate material contained therein and effect size reduction of the material. The agitator can effect a mechanical impact to the material in order to break and divide the material into smaller piece parts. The agitator can be configured to reduce the material to a sufficient small size to achieve a liquefied solution. The agitator can be a rotating blade type member that repetitively severs the material into smaller piece parts. However, the agitator need not be like a blade type member, as it can be a member that is not blade like, but is designed to mechanically impact the material repetitively with a rigid member, high pressure fluid or other agitation source and break it into smaller pieces. In one embodiment the apparatus the vessel can be designed with a chamber that can be pressurized and a heat source such that the mixture can be heated to a temperature in the range of approximately 250 to 308 degrees F. at its equivalent saturated pressure and held approximately at that temperature for a period of approximately one to three hours to effect sterilization of the liquefied mixture. One embodiment of the apparatus can also include a vessel having an internal mounting fixture adapted for inserting biological samples into a biological test chamber. The fixture can be designed such that it can be positioned in the liquid while maintaining agitator operation.

Various embodiments of the method and apparatus can provide a less expensive and a more simplified approach to sterilizing and disposing of infectious material that is clearly needed in the industry, that is safe and that is more environmentally friendly and less expensive than existing sterilization methods and their subsequent disposal. Also, various embodiments of the invention involve a method and apparatus for sterilizing animal carcasses, parts, infectious viruses and bacteria, human corpses, human parts, biological spores and other biological matter and is intended to comply with all governmental laws and regulations, national and provincial/ state, applicable to disposal of such biological wastes.

These and other advantageous features of the present invention will be in part apparent and in part pointed out herein below. Further, U.S. Provisional Patent Application Ser. No. 61/405,979, filed Oct. 22, 2010 entitled THERMAL TISSUE AUTOCLAVE, the entirety of which is hereby incorporated herein by reference.

BRIEF DESCRIPTION OF THE DRAWINGS

For a better understanding of the present invention, reference may be made to the accompanying drawings in which.

DRAWING ITEM LISTING

100 Sterilization System
102 Lid

103 Lid Hinge
104 Pressure Indicator
105 Lid Opening Cylinder
106 Monitoring Port
108 Temperature Sensor
110 Heating/Cooling Jacket
112 Discharge Valve
114 Discharge Valve Actuator
116 Thermal Liquid Inlet Port
118 Temperature Sensor
120 Gear Reducer
122 Drive Motor
124 Mounting Bracket
126 Operating Vent Pipe
128 Lid Locking Cylinder
130 Vapor Outlet
132 Combination Water and Caustic Inlet Port
133 Safety Vent Outlet
134 Thermal Liquid Outlet Port
135 Operating Vent Outlet
137 Pressure Transmitter
202 Port For High-Level Control (304)
204 Port For Safety Vent Outlet (133) and Pressure Transmitter (137)
206 Pressure Vessel Entry
302 Decontamination Product Valve
304 High-Level Control at Port (202)
305 Bio Test Port
306 Pressure Transmitter
308 Valve Actuator
402 Valve Actuator
404 Valve Actuator
802 Drive Transfer Seal Assembly
804 Arm Mount
806 Arm Mount
808 Mounting Ring
810 Agitator Arm
812 Agitator Blade
814 Pressure Vessel Lower Chamber
816 Drive Shaft
904 Discharge Port While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DETAILED DESCRIPTION OF INVENTION

According to the embodiment(s) of the present invention, various views are illustrated in FIG. 1-10 and like reference numerals are being used consistently throughout to refer to like and corresponding parts of the invention for all of the various views and figures of the drawing. Also, please note that the first digit(s) of the reference number for a given item or part of the invention should correspond to the Fig. number in which the item or part is first identified.

One embodiment of the present invention comprising pressurized heat treatment and agitation system teaches a novel apparatus and method for sterilizing infectious material where one embodiment of the method can include placing biologically infected animal carcasses, tissue, bones and innards or other infectious material into a pressure vessel. One embodiment of the method can further include adding a quantity of water that can be from approximately 0% to approximately 20% of the tissue weight into the pressure vessel. Further, the method can include heating externally the chamber containing the material to bring the temperature of the vessel interior to the range from approximately 250 to approximately 308 degrees F. at a pressure ranging from approximately 0 to approximately 60 psig. This can be continued to effect degrading the waste material at these elevated temperatures and pressures. One embodiment of the process can include maintaining the environment of elevated temperature for a time period from approximately 0 to approximately 4 hours to raise the actual temperature of the tissue and other material, thereby effectively softening any biological tissue.

Agitating the material with an agitator can perform sizing the material thereby producing non-caustic discharge producing bone chards less than 1.5 inches and tissue fibers of diameters less than 0.015 inches. The process can be performed such that the solids are dispersed in the homogeneous mixture. If any caustic material is injected, it can be injected such that the discharged material has indistinguishable characteristics.

One embodiment of the method can include placing the animal carcasses, tissue, bones and innards into the pressure vessel and adding a quantity of water; between 0% and 20% of the tissue weight in the vessel. The vessel can be heated externally to bring the temperature of the vessel interior to the range of 250 to 308 degrees F. These elevated temperature and pressure conditions are conducive to completely degrading the waste material. The pressure range over the profile may range from 0 to 60 psig.

The tissue, bones and other waste matter, which may contain infectious viruses, bacteria, spores or prions can be allowed to remain in this environment of elevated temperature for a time period of 0 to 4 hours to raise the actual temperature of the tissue and other material. This period effectively softens the tissue and bone.

The agitator is designed to effect sizing reduction of any infectious material or waste including tissue, tendons, muscle and bones. The effectively reduced non-caustic discharge produces bone chards less than approximately 1.5 inches in diameter and tissue fibers of less than approximately 0.015 inches in diameter. If an option is exercised to introduce caustic injected material, the discharge mixture can have indistinguishable characteristics and dispersed solids. The effectively reduced material can be homogeneous and wax-like.

The agitator and chamber design can be such that a method and apparatus can be included to attach and detach biological sample containers that can be used for validating that the material has been adequately sterilized. One embodiment of such a method and apparatus is to provide an agitator without a centerline shaft and having an elongated bar like member with a circular shape or semi-circular shape or a member having a hemispherical configuration and having shafts on opposing sides for effecting rotation of the member. This embodiment avoids a problem that could be experienced if a rotor blade or implement having a center-line drive shaft is utilized. If such a center-line rotor is used, it could obstruct or hinder the insertion of the infectious material. With a center-line system, an operator when inserting material would have to navigate around the center-line drive shaft and rotors. The embodiment as described herein eliminates the center-line drive shaft and center-line rotor. The semi-circular or circular rotor can be position in the horizontal plane when inserting material such that the vessel has a central clear pathway from the loading hatch to the bottom of the vessel.

The agitator can be powered to provide sufficient impact force to thoroughly size reduce and mix the combination of water, solids, and fats. The agitator can also be designed to extend its reach to the interior perimeter of the inside walls of the chamber in order to clean the heat transfer surfaces of the chamber to insure satisfactory heat transfer coefficients. The agitator can be configured to provide a slight scraping or near scraping action to keep material from accumulating along the perimeter. One embodiment of the apparatus can also have an agitator configured and oriented to push or urge the final fibrous material to a centerline discharge port. Also, the agitator drive can include a variable frequency controller, which can allow the agitator to be started at a low rpm, for example one revolution per minute, and advance to approximately 20 revolutions per minute. Starting at a lower speed when the material parts are larger in one embodiment can allow for a greater torque at lower speeds and/or can reduce shock to the drivetrain.

One embodiment of the method and apparatus can provide a chamber with an internally mounted fixture, capable of inserting biological samples. The fixture can be designed such that it can be positioned in the liquid while maintaining agitator operation.

For one embodiment of the method, upon completion of the heat-up phase, the agitator can be started and run continuously for approximately 2 to 4 hours during which time the material goes through size reduction and physical milling to create a water-like mixture of suspended solids and water. As an option, during this phase small quantities of caustic, NaOH or KOH, may be injected into the mixture to effect saponification of the fatty acid derivatives and further molecular reduction of the proteins. This option is designed to maintain a pH of between about approximately 7 and 10.99. Less than 4% (less than 4% of the original tissue weight) of caustic solution can be introduced.

With or without the saponification step, this phase provides a complete sterilization of all elements of the material; assuring log 6 reduction criteria of infectious matter. The liquid is then available for two optional discharge modes. Existing technology typically injects a caustic portion into the initial load and then uses the dehydration on the digestate (includes animal tissue, additional water and caustic) to remove the water and produce a solidified mass. The difficulty with this is that the caustic saponifies the fats into soaps. These soaps have a high surface tension which can then create foam or belching during the dehydration phase, carrying solids and raising the Biological Oxygen Demand (BOD) level of the reclaimed water. This results in a very undesirable by-product which can be difficult to dispose of and can cause mechanical difficulties of blockage in pipes, heat exchangers and other restrictive devices over time.

One embodiment of the process design uses a unique introduction of a caustic to avoid the foaming issue and dehydrates the solids to a homogeneous solid mass and produces a clear, "lower BOD" reclaimed water, acceptable for discharge directly to a municipal waste water treatment facility. This embodiment of the process can raise the product up to 308 degree F. and agitate the product, which can provide size reduction of the animal tissue and bones into a water-like mixture of suspended solids. The pressure of the vessel can be reduced to approximately atmospheric pressure to effect a dehydration of the mixture and a step of collecting reclaimed water can be accomplished by a water condenser. One embodiment of the system can include system control logic capable of automatically determining the dehydration end point rather than using a form of trial and error methodology. With the addition of the condenser function, the over all system can be either a "wet" or "dry" discharge system. The condenser can be a direct contact condenser, an externally cooled condenser or a combination of both to achieve condensing and collection of the reclaimed water.

This embodiment of the process can introduce the caustic at end of the dehydration thereby allowing digestion and saponification to occur at lower levels of water content. The surface tension of the liquid mixture is greatly increased and attempts to distill water would result in carry-over of fatty acids and other material resulting in elevated BOD. The resultant discharged sludge can be very viscous and homogeneous and flowable at elevated temperatures and then solidifies upon cooling. A visual monitoring system can also be utilized to witness the process.

For an embodiment of the method and apparatus having a liquid discharge design, the vessel's thermal liquid can be cooled to indirectly cool the internal liquid. Upon cooling the internal liquid to less than about approximately 140 degrees F., the bottom discharge valve can be opened to discharge the sterile liquid to sewer or other appropriate receiver. The bottom discharge vale can be "flush mounted" such that there is no pipe to flange to valve interface creating a "dead leg" in the pipe area that is not heated thereby potentially creating an area where the liquid potentially could not be properly sterilized.

For an embodiment of the method and apparatus having a solid discharge, the vessel can continue the heating process and allow the pressure to be reduced to atmospheric conditions and released saturated vapors can be directed to a condenser where the water vapors are condensed and collected. This phase is tissue mass load size dependent and may operate from approximately 1 to 7 hours. The water collected may be partially recycled into the next load for re-use thereby improving environmental operation; and helping to meet "green" operational criteria. At its completion, the internal material is now a fibrous, sludge-like matter. It can be discharged through the bottom discharge valve. The discharge residue can be brown in color and can have small portions of fatty liquid which quickly solidifies into a wax-like product. The fibrous solids, upon cooling, are a rigid, solid mass.

One embodiment of the method and apparatus can utilize a monitoring system to visually monitor the operation of the process. The variety of animals and their respective variance in water to tissue ratio precludes an accurate mass or volume determination exact enough to determine process completion. The visual monitor provides such a method where repeatable interpretation of residue can be provided.

Figure 1:
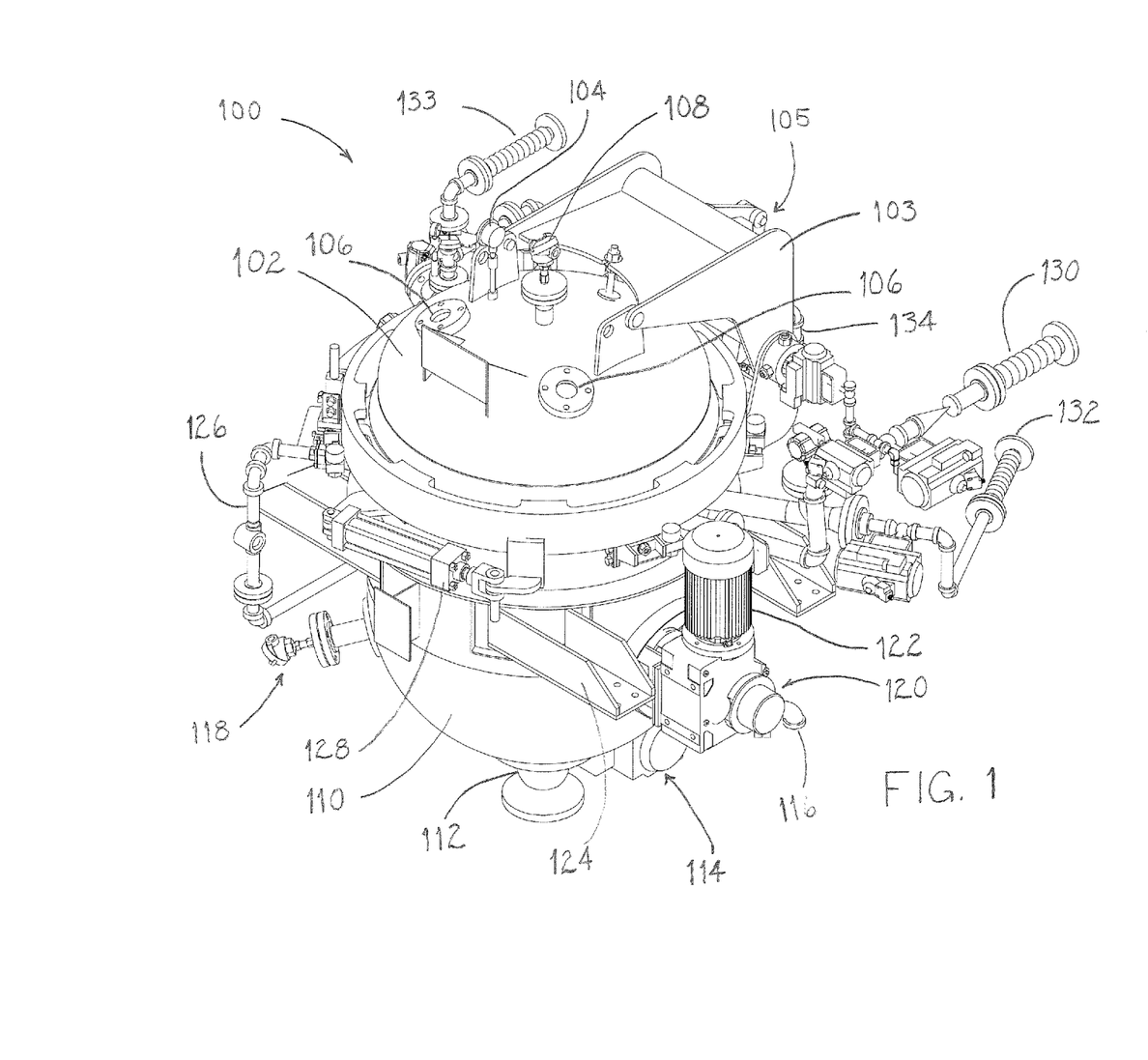
FIG. 1 is a left perspective illustration of an embodiment of a sterilization system.

The details of the invention and various embodiments can be better understood by referring to the figures of the drawing. Referring to FIG. 1, a left perspective illustration of an embodiment of a sterilization system is shown. This view illustrates the pressure vessel having the Lid 102 in the closed position. The Lid 102 can be sealed and locked using the Lid Locking Cylinder 128. If the Lid Locking Cylinder 128 is de-actuated, the Lid Opening Cylinder 105 can be utilized to retract the Lid 102 to the open position. The lid as shown in its closed position and sealed is the operating position of the lid. When the lid is sealed and closed, the vessel can be pressurized. In order to allow internal viewing of the vessel during operation, two monitoring ports 106 are provided. Cameras or other viewing mechanisms or systems can be mounted to these monitoring ports for viewing and/or recording the interior of the chamber when in operation.

Various sensors are utilized to monitor the operational conditions of the vessel. The sensors can include Temperature Sensors 108 and 118 which are adapted to monitor the internal temperature of the vessel. A Pressure Indicator 104 can also be utilized to monitor the interior pressure of the vessel. The various sensors can be communicably linked to a control system having a controller whereby temperature and pressure data and other sensor data can be transmitted to the control system which can in turn control the inputs to the sterilization system to vary the operational profile based on the data provided by the sensors. For example, the controller can control a heating system for regulating the temperature of the thermal liquid and can control the input of thermal liquid into the heating/cooling jacket in order to control the temperature within the vessel and thereby control the temperature of the material.

When the system is not in operation the Lid Opening Cylinder 105 can be utilized to retract the Lid Hinge to thereby open the Lid 102. The Heating/Cooling Jacket 110 can be controlled by a controller system to heat or cool the interior of the vessel. The interior of the vessel can be heated or cooled to the desired temperature during the operational profile and once the operational profile is completed any sterilized material can be discharged through a Discharge Valve 112. The controller can control the Discharge Valve Actuator to open the discharge valve to dispense of the sterilized material within the vessel.

During operation an Agitator Arm and Agitator Blade can be utilized to reduce the size of any waste material. The Actuator or Agitator can be powered by a Drive Motor and Gear Reducer 122 and 120 respectively. The control system can cause thermal liquid to be input through the Thermal Liquid Inlet Port 116 at a desired temperature to cause the Heating/Cooling Jacket to arrive at the desired temperature for the purpose of controlling the temperature of the interior of the vessel. Water and caustic material can be added to the interior of the vessel utilizing the Combination Water and Caustic Inlet Port 132. Therefore, water and caustic material can be added to any infectious waste inserted within the vessel and the Heating/Cooling Jacket can be utilized to control the temperature of the interior of the vessel to thereby control the temperature of the infectious waste material and water contained therein.

The control system can monitor the interior pressure and temperature of the vessel and thereby control the temperature profile utilizing the Thermal Liquid Input Port 116. During operation the Drive Motor 122 can be powered to drive the agitator to reduce the size of any infectious waste material. The system is also shown having a Vapor Outlet 130 which allows vapor to escape from the vessel while maintaining the desire pressure. The sterilization system also has a Safety Vent Pipe to allow pressure to be released from the interior of the vessel. Also Operating Vent Outlet 135 and Safety Vent Outlet 133 are provided. The thermal liquid can be discharged at the end of an operational cycle from the Heating/Cooling Jacket utilizing the Thermal Liquid Output Port 134. The sterilization system can be properly mounted using the Mounting Brackets 124.

Figure 2:
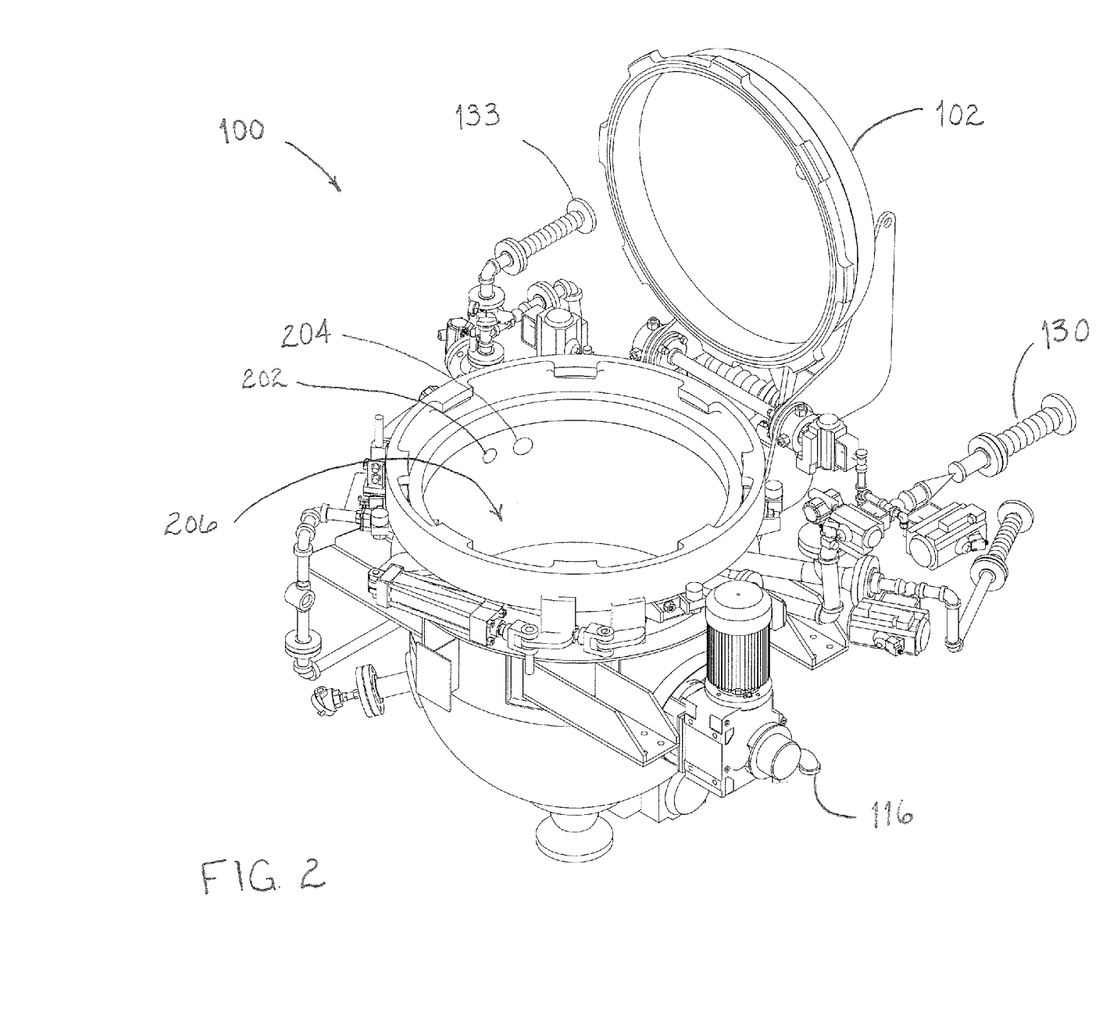
FIG. 2 is another left perspective illustration of the sterilization system.

Referring to FIG. 2, a another left perspective illustration of the sterilization system is shown. This illustration shows the Lid 102 in the open position. The Pressure Vessel Entry 206 is shown through which infectious waste material can be inserted into the pressure vessel. This interior view also reveals two Ports 202 and 204. The ports are for high level control and safety vent outlet respectively. With the lid in the open position and the agitator oriented in a horizontal position, the material to be sterilized can be loaded.

Figure 3:
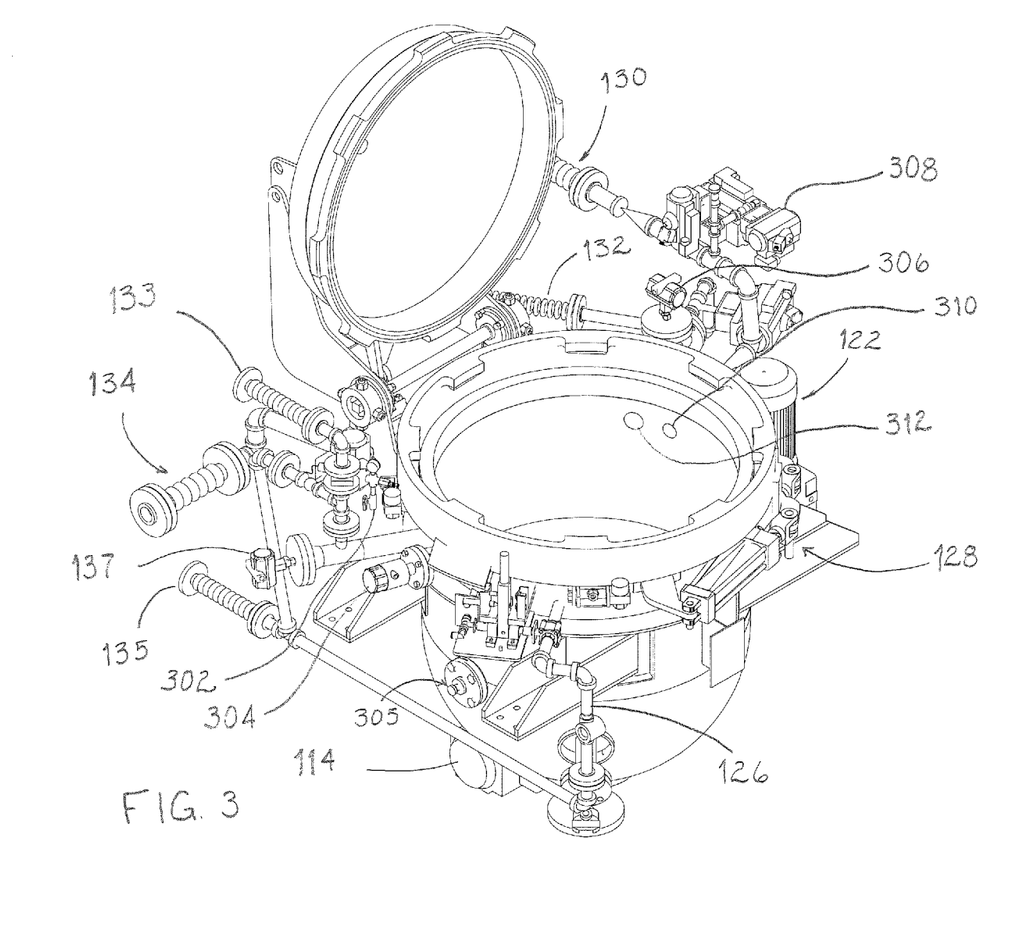
FIG. 3 is another right perspective illustration of the sterilization system

Referring to FIG. 3, a right perspective illustration of the sterilization system is shown. This view again shows the Lid in the open position revealing the interior of the pressure vessel. This left perspective view reveals a Bio-Test port 305 through which biological samples (biological spore strips) can be inserted to validate sterilization efficacy. An Decontamination Product valve 302 is also shown. Various other control and sensing devices including pressure transmitter 306 and High-Level Control are shown. Various Ports, the Vapor Outlet 310 and water and caustic inlet 312 are also shown.

Figure 4:
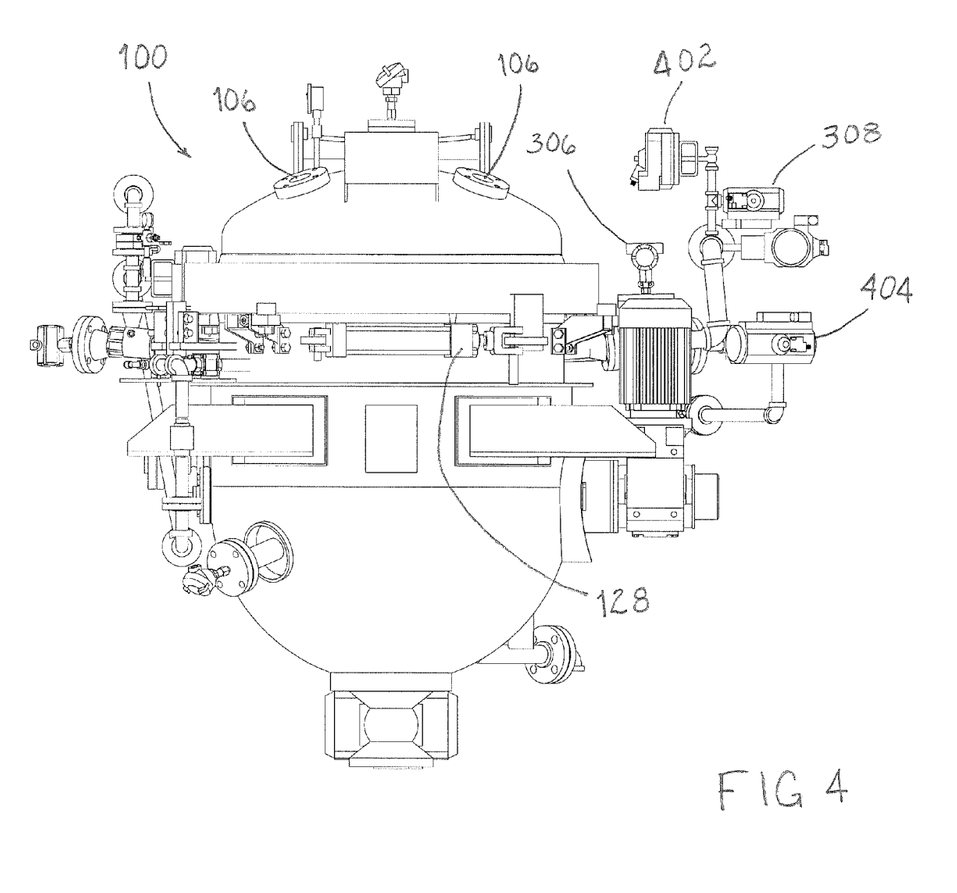
FIG. 4 is a front view of the sterilization system.

Referring to FIG. 4, a front view of the sterilization system is shown. This front view again shows the sterilization system with the Lid 102 in the closed position. Valve actuators 402, 308 and 404 are shown. The Viewing Ports 106 are also shown. The Lid Locking Cylinder 128 can be controlled by the control system to be actuated to seal the lid. A lid sensor can be utilized to monitor the seal and if the seal is disrupted a signal can be sent to the control system which can reestablish the seal or shut down the system as appropriate.

Figure 5:
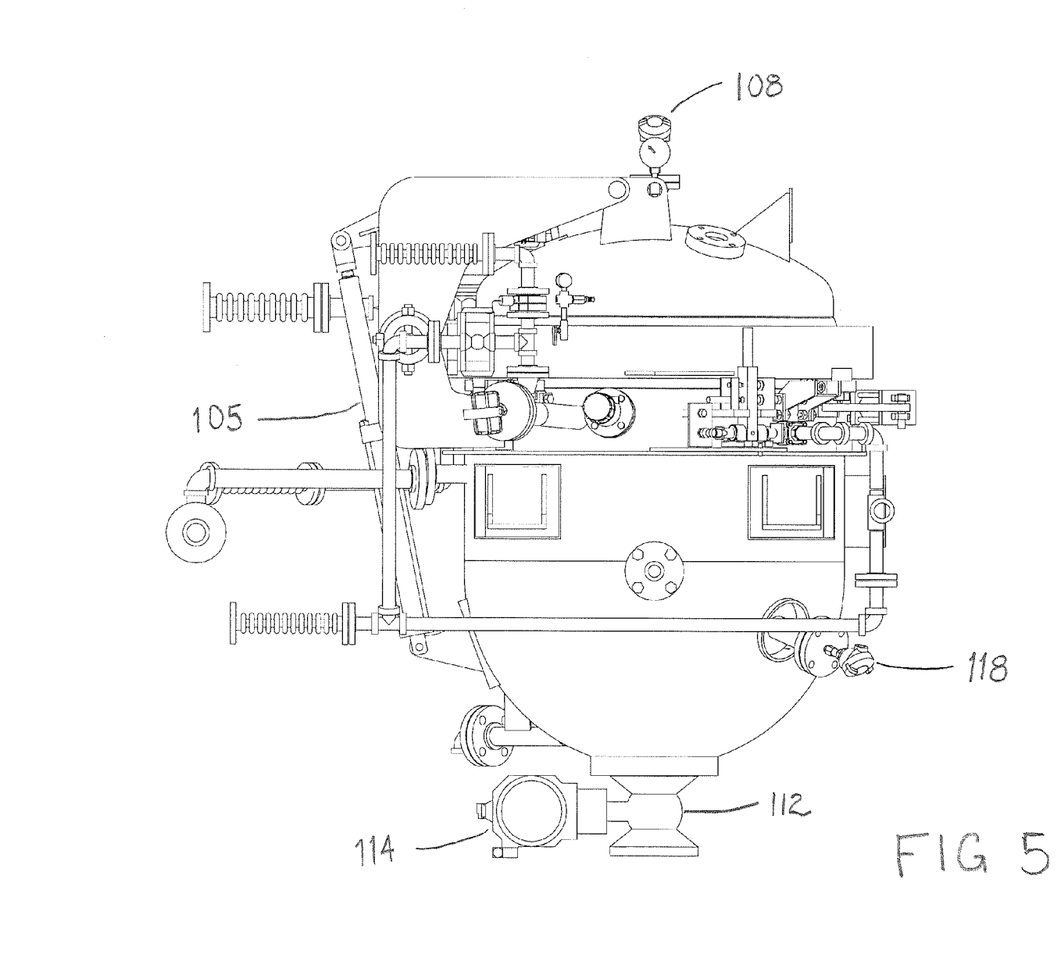
FIG. 5 is a right side illustration of the sterilization system.

Referring to FIG. 5, a right side illustration of the sterilization system is shown. The right side view again reveals the various components including the Temperature Sensors 108 and 118. Another view of the Lid Opening Cylinder 105 is also shown. The Cylinder 105 is shown in the extended position such that the Lid Hinges are positioned to close the lid in the sealed position.

Figure 6:
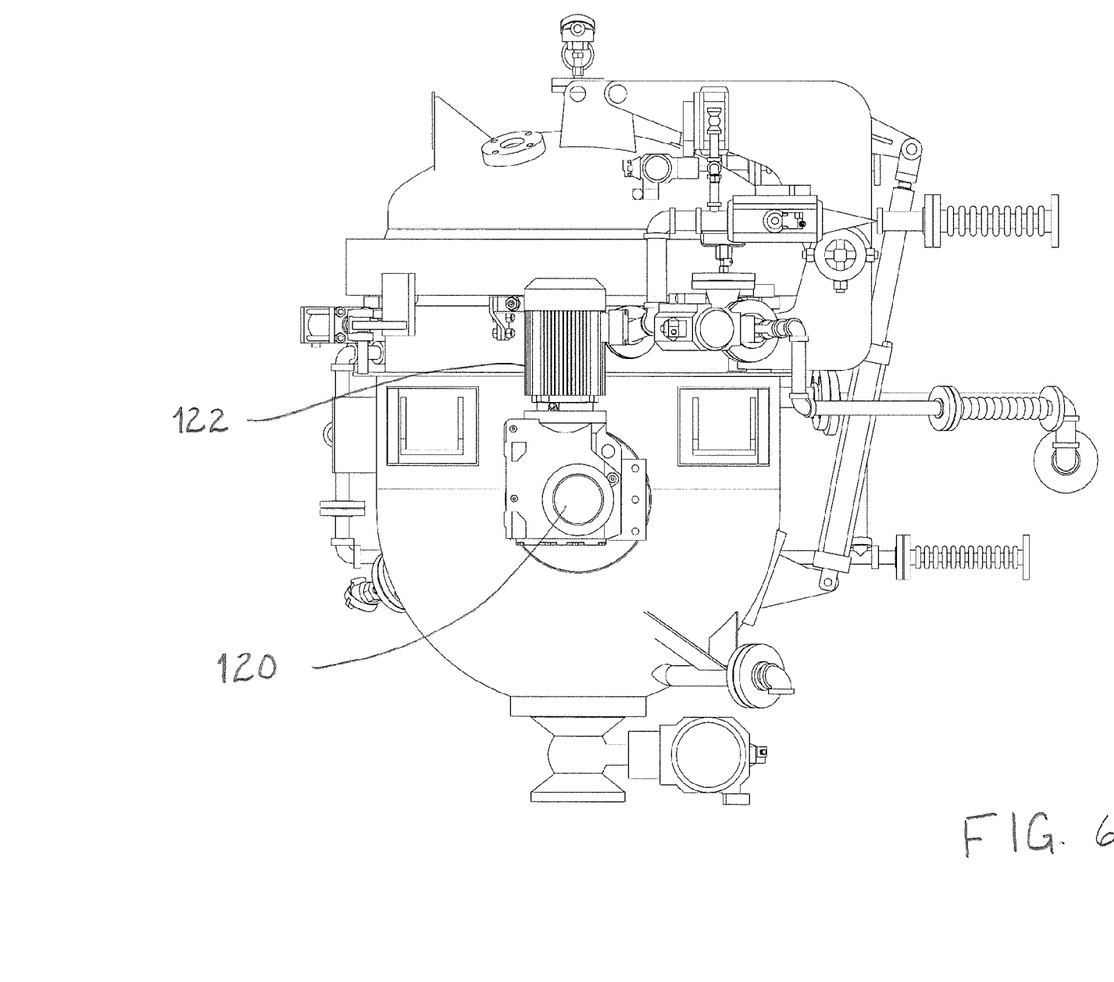
FIG. 6 is a left side illustration of the sterilization system.

Referring to FIG. 6, a left side illustration of the sterilization system is shown. This view again reveals the Drive Motor 122 and the Gear Reducer 120. During operation the control system can control the Drive Motor 122 to drive the Agitator Arm and Agitator Blades at various and varying speeds to affect size reduction of any infectious waste solids inserted within the vessel.

Figure 7:
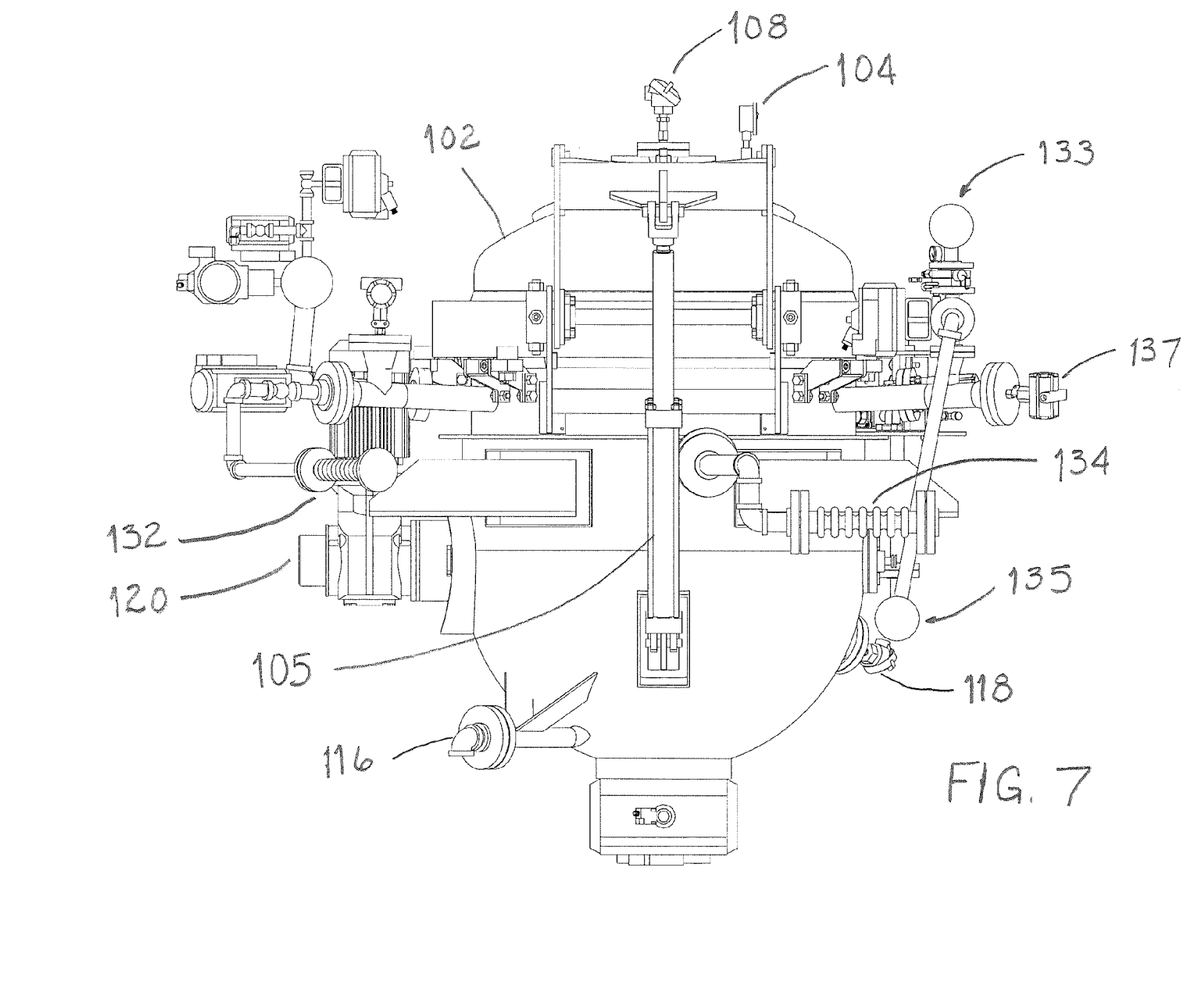
FIG. 7 is a rear illustration of the sterilization system.

Referring to FIG. 7, a rear illustration of the sterilization system is shown. The rear view again reveals the Lid Opening Cylinder 105 shown in the extended position to thereby close the Lid. The Thermal Liquid Input Port 116 is also shown which can be utilized to input thermal liquid into the Heating/Cooling Jacket to thereby control the temperature of the vessel.

Figure 8:
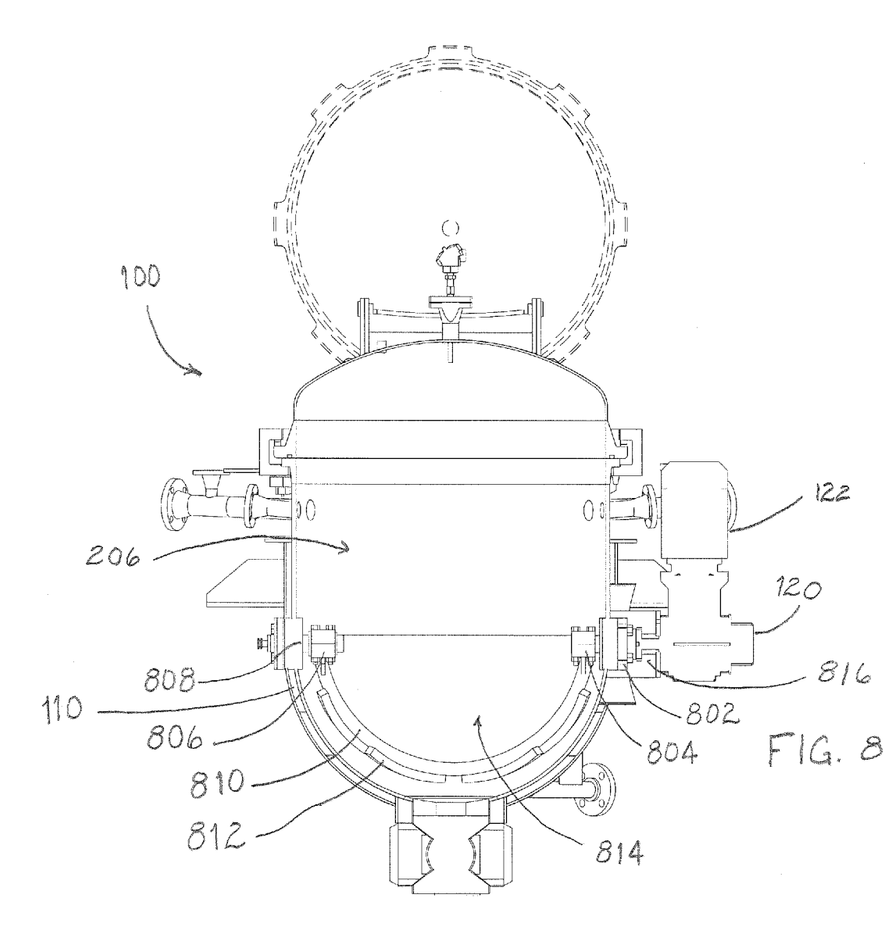
FIG. 8 is a sectional view of the sterilization system.

Referring to FIG. 8, a sectional view of the sterilization system is shown. This sectional view reveals the interior of the vessel. Again the Pressure Vessel Entry 206 is shown through which infectious waste material can be inserted. This view also reveals one embodiment of an Agitator Arm and Agitator Blade 810 and 812 respectively. An end of an agitator arm can be powered by the Drive Motor 122 and the Gear Reducer 120. The Drive Motor can be controlled to vary the speed and torque of the agitator to affect size reduction of any infectious waste material. The Gear Reducer can drive the Drive Shaft 816 which is sealed by the Drive Transfer Seal Assembly 802. The agitator can be mounted by Arm Mounts 804 and 806. The opposing side of the Agitator Arm can be mounted on the Mounting Ring 808 which allows rotation of the agitator as needed. Agitator Blade 812 as shown can be designed to be in a fixed position and/or can be designed to vary its position by rotating about an axis which is perpendicularly oriented with respect to the agitator arm.

Figure 9:
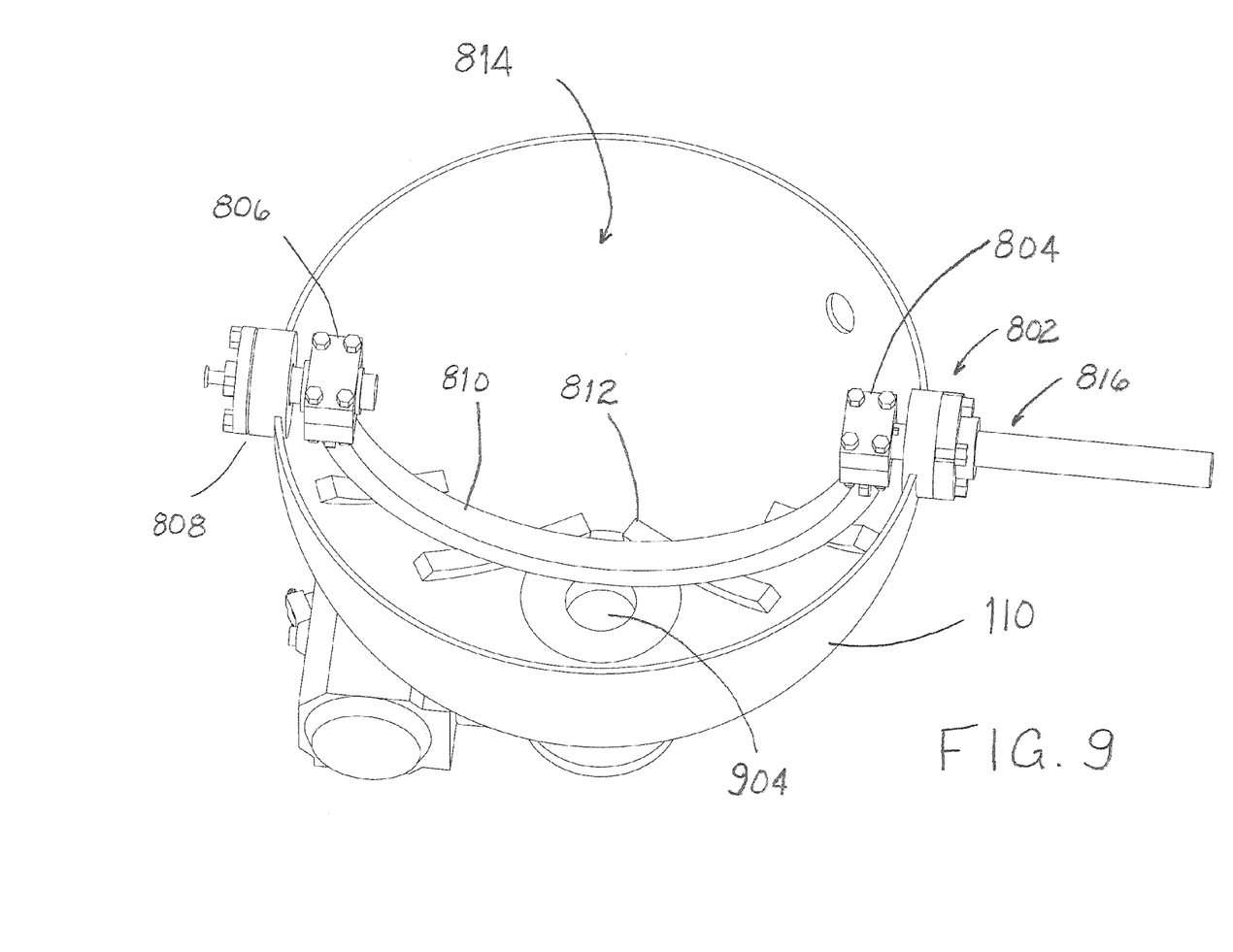
FIG. 9 is an illustration of the vessel chamber.

Referring to FIG. 9, an illustration of the vessel chamber is shown. This view reveals the interior of the Pressure Vessel Lower Chamber 814. The design of the Agitator Arm is such that the center pathway of the Pressure Vessel Entry is not obstructed by the agitator or by any of it components when it is positioned in a horizontal orientation. Therefore infectious waste material can be inserted within the chamber without attempting to navigate about a center agitator. The discharge port 904 is also shown at the bottom of the vessel chamber.

Figure 10:
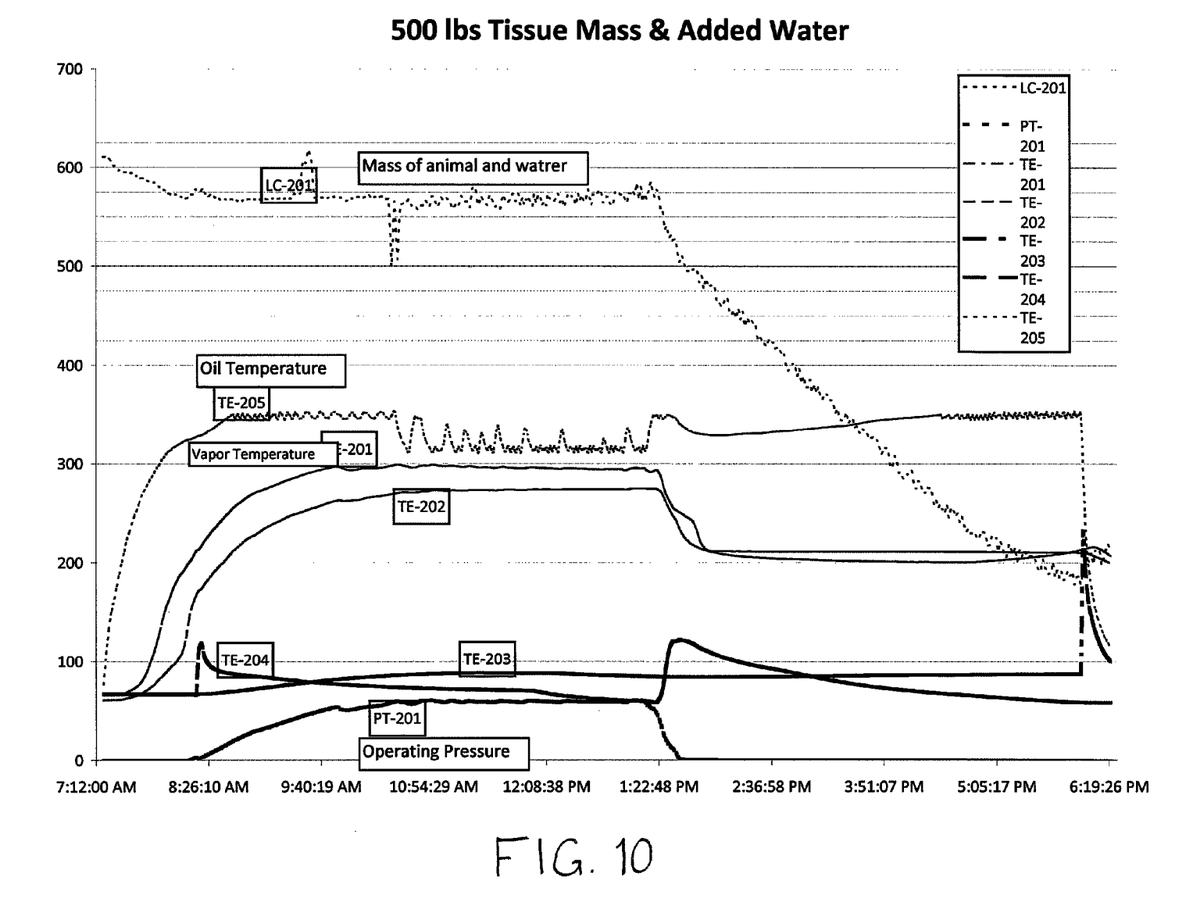
FIG. 10 is a graphical illustration of a typical operational profile.

Referring to FIG. 10, a graphical illustration of one embodiment of a operational profile is shown. This graphical illustration is an illustration of one embodiment of an operational profile for treating five-hundred pounds of tissue mass and added water.

The various embodiments of the method and apparatus for sterilizing infectious waste and examples shown above illustrate a novel method and apparatus that provides a less expensive and a more simplified approach to sterilizing and disposing of infectious material that is clearly needed in the industry, that is safe and that is more environmentally friendly and less expensive than existing sterilization methods and their subsequent disposal. A user of the present invention may choose any of the above embodiments, or an equivalent thereof, depending upon the desired application. In this regard, it is recognized that various forms of the subject sterilization method and apparatus could be utilized without departing from the spirit and scope of the present invention.

As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the sprit and scope of the present invention.

Other aspects, objects and advantages of the present invention can be obtained from a study of the drawings, the disclosure and the appended claims.

What is claimed is:

1. A method for sterilizing infectious waste comprising the steps of:
    adding water in a pressure vessel containing infectious waste material including a combination of tissue and other material to form a pH neutral waste combination of tissue and other material;
    heating the pH neutral water combination of tissue and other material by externally bringing a temperature of the vessel interior chamber to a range of about 250 to 308 degrees F. at a pressure in the vessel interior chamber in a range of about 0 to 60 psig;
    maintaining the temperature of and pressure in the vessel interior chamber for a time period of about 0 to 4 hours to raise the actual temperature of the pH neutral water combination of tissue and other material, effectively degrading and softening the infectious waste material, and maintaining the pH neutral water combination of tissue and other material at a pH of approximately 7; and
    size reducing the infectious waste material in the pH neutral water combination of tissue and other material with an agitator producing a non-caustic mixture of the tissue and other material.

2. The method for sterilization as recited in claim 1, where water is added in a variable ratio and in a range of about 0% and 20% by weight of the total material in the pressure vessel.

3. The method for sterilization as recited in claim 2, further comprising the steps of:
    reducing the pressure of the vessel to approximately atmospheric pressure to effect a dehydration of the mixture collecting reclaimed water by a water condenser.

4. The method for sterilization as recited in claim 2, further comprising the steps of:
    introducing of a caustic after producing the non-caustic combination of tissue and other material to avoid a surface tension issue and dehydrating the solids to a homogeneous solid mass and producing a clear reclaimed water having a BOD lower than before introducing the caustic and dehydrating.

5. The method for sterilization as recited in claim 4, further comprising:
    raising the product up to 308 deg F. and agitating, thereby providing size reduction; and
    introducing a caustic at the end of a dehydration, thereby allowing digestion and saponification to occur, thereby reducing the surface tension issue, resulting in a final resultant discharged sludge.

6. The method for sterilization as recited in claim 5, further comprising:
    allowing the final resultant discharge to cool and solidify.

7. The method for sterilization as recited in claim 5, wherein the infectious waste material contains tissue and bone and wherein agitating with the agitator produces bone chards less than about 1.5 inches in diameter and tissue fibers of diameters less than about 0.015 inches in diameter.

8. The method for sterilization as recited in claim 5, wherein the caustic injected mixture of tissue and other material has indistinguishable characteristics and evenly dispersed solids and all material is homogeneous animal and where tissue and bones are in a mixture of suspended solids.

9. The method for sterilization as recited in claim 3, further comprising the steps of: indirectly cooling the dehydrated mixture, whereby, upon cooling the dehydrated mixture to less than 140 degrees F., discharging sterile liquid to a discharge receiver.

10. The method for sterilization as recited in claim 5, further comprising the steps of:
    maintaining the product at 308° F. and allowing the pressure to be reduced to atmospheric conditions and releasing saturated vapors directed to a condenser where water vapors are condensed and collected;
    operating for from 1 to 7 hours;
    recycling at least a portion of condensed water into the next load for re-use thereby improving environmental operation, creating an internal material that is now a fibrous solid;
    discharging the internal material; and
    allowing the fibrous solid, upon cooling, to become a rigid, solid mass.

11. The method for sterilization as recited in claim 10, further comprising the steps of:
    discharging the solid mass to an appropriate receiver.

12. The method for sterilization as recited in claim 5, further comprising the steps of:
    monitoring with a visual monitoring system.

* * * * *